US00PP12811P2

(12) United States Plant Patent
Jones

(10) Patent No.: US PP12,811 P2
(45) Date of Patent: Jul. 30, 2002

(54) NEMESIA PLANT NAMED 'PENSUG'

(76) Inventor: Jimmy Jones, 14 Avondale Rd. Pontneywod, Cumrangwent, S. Wales NP26 3AU (GB)

( * ) Notice: Subject to any disclaimer, the term of this patent is extended or adjusted under 35 U.S.C. 154(b) by 0 days.

(21) Appl. No.: 09/728,154

(22) Filed: Dec. 2, 2000

(51) Int. Cl.[7] ..... A01H 5/00

(52) U.S. Cl. ..... Plt./263
(58) Field of Search ..... Plt./263

*Primary Examiner*—Bruce R. Campell
*Assistant Examiner*—A. Para

(57) ABSTRACT

A new and distinct cultivar of Nemesia plant named 'Pensug' that is characterized by uniform and abundant flowering, pure-white fragrant flowers, and a compact habit, setting it apart from all other existing varieties of Nemesia known to the inventor.

3 Drawing Sheets

CROSS-REFERENCES TO RELATED APPLICATIONS

This application is related to another application entitled Nemesia Plant Named 'Penmys', having the same inventor as the present invention.

BACKGROUND OF THE INVENTION

The present invention relates to a new and distinct cultivar of Nemesia, that will be referred to hereinafter by the cultivar name 'Pensug'. The new Nemesia was selected in Netherwent, Caldicot, South Wales on May 1, 1998 by the inventor. The parents are of hybrid origin and have not themselves been released, but are intermediate seedlings in the selection process. The first crosses were made in South Wales by the inventor in 1997 with plants selected from a long term Nemesia breeding program.

Breeding was carried out by cross pollination of Nemesia hybrids and seedling selection was made on the basis of producing a white flowering Nemesia with numerous flowers, scented flowers, uniform flowers and compact habit.

The combined characteristics of the new invention 'Pensug' are unique. 'Pensug' is distinguished from all other cultivars, in this color range, by its abundant pure-white, scented and uniform flowers and its compact habit, making 'Pensug' more fragrant, compact, and uniform in flowering than any other white variety. The closest comparison cultivar is Nemesia 'Innocence' (unpatented). The new cultivar is distinct from 'Innocence' (unpatented) in its profuse flowering, larger flower, upright habit and greater height.

'Pensug' was first asexually propagated by the inventor on May 1, 1998 in Netherwent, Caldicot, South Wales and has been found to be true to type after many cycles of vegetative cuttings since that time.

SUMMARY OF THE INVENTION

The following traits have been repeatedly observed and represent the distinguishing characteristics of the new Nemesia cultivar. 'Pensug' is fragrant, more floriferous, more compact in habit and more uniform in flowering than any other white Nemesia. 'Pensug' is distinct from 'Innocence' in its taller, more upright habit and larger pure white flowers.

In combination these attributes distinguish this cultivar from all other existing varieties known to the inventor.

BRIEF DESCRIPTION OF THE DRAWINGS

The accompanying color photographs illustrate the overall appearance of the new cultivar.

Sheet 1 illustrates the habit and flowering.

Sheet 2 compares 'Innocence' (unpatented) on the left to 'Pensug' on the right.

Sheet 3 shows a close-up view of the flowers. All photographs are taken of plants grown in two-gallon containers. The prints were made using conventional photographic techniques and although colors may appear different from actual colors due to light reflectance, they are as accurate as possible by conventional photography.

BOTANICAL DESCRIPTION OF THE PLANT

The following is a detailed description of the Nemesia cultivar named 'Pensug'. Data was collected in Arroyo Grande, Calif. from 9-month-old plants grown in two-gallon containers. Phenotypic differences may be observed with variations in environmental, climatic, and cultural conditions. The color determinations are in accordance with The Royal Horticultural Society Colour Chart except where general color terms of ordinary dictionary significance are used. The growing requirements are similar to other Nemesias and 'Pensug' is resistant to common pests and disease.

Botanical classification: Nemesia hybrid.
Common name: Nemesia.
Use: Bedding, patio plant or hanging basket.
Parentage: Intermediate Nemesia seedlings from unnamed hybrids used in the selection process.
Propagation: Tip cuttings.
Plant habit: Erect and upright.
Form: Dense and compact.
Branching habit: Freely branching with lateral branches and secondary laterals.
Dimensions of plant: 54 cm. in height and 30 cm. in width.
Type: Vegetative annual.
Time to initiate roots: Approximately 16 days at temperatures of 21° Centrigrade.
Time to develop roots: Approximately 28 days at temperatures of 21° Centrigrade.

Rooting habit: Numerous and fine.
Special needs: Root cuttings on bottom heat at approximately 19° Centigrade in greenhouse.
Vigor: Moderate.
Hardiness: USDA Zone 9.
Stem:
*Stem shape.*—Quadrilateral.
*Stem surface.*—Glabrous.
*Stem color.*—137C.
*Stem texture.*—Flexible and has corner ridges.
*Internode length.*—2 cm. to 5 cm. between nodes.
Foliage:
*Leaf shape.*—Lanceolate.
*Leaf division.*—Simple.
*Apex.*—Acute.
*Base.*—Acuminate.
*Margins.*—Slightly serrate.
*Texture.*—Flexible, smooth and dull.
*Surface.*—Glabrous.
*Arrangement.*—Single, opposite and generally symmetrical.
*Lateral branch length.*—10 cm. to 14 cm. in length.
*Lateral branch width.*—2 mm. in width.
*Number of leaves per lateral branch.*—Approximately 10 to 12 leaves.
*Petiole length.*—Approximately 3 mm. to 4 mm. in length.
*Petiole width.*—Approximately 1 mm. in width.
*Petiole color.*—138A,B.
*Leaf color upper surface* (*mature*).—137B.
*Leaf color lower surface* (*mature*).—137C.
*Leaf color upper surface* (*young*).—137A.
*Leaf color lower surface* (*young*).—137B.
*Venation upper surface.*—Mid-vein slightly depressed.
*Venation lower surface.*—Mid-vein slightly protruding.
*Color of vein* (*upper surface*).—137B.
*Color of vein* (*lower surface*).—137C.
Flowers:
*Flowering season.*—Spring to late autumn.
*Fragrance.*—Pungent honeysuckle-like scent.
*Self-cleaning or persistent.*—Self-cleaning.
*Flower length.*—1.5 cm. in length.
*Flower diameter.*—1.5 cm. in diameter.
*Type.*—Terminal inflorescence.
*Habit.*—Cluster.
*Quantity of flowers.*—Floriferous. Approximately 10 to 12 flowers per terminal cluster.
*Petals.*—Four petals fused at base and basal fifth bi-labiate petal modified with nectar spur.
*Petal length.*—Fused petals and fifth petal are both 9 mm. in length.
*Petal width.*—Fused petals 1.5 cm in width and fifth petal 1.25 cm. in width.
*Surface.*—Smooth.
*Flower shape.*—Personate with cleft in middle of palate.
*Flowering time.*—Diurnal.
*Palate color.*—2A.
*Palate dimensions.*—3 mm. in length and 2 mm. in width.
*Petal margins.*—Entire.
*Petal color* (*upper surface*).—155D.
*Petal color* (*lower surface*).—155D.
*Peduncle length.*—3.5 cm. in length.
*Peduncle width.*—2 mm. in width.
*Peduncle texture.*—Flexible and slender.
*Peduncle color.*—144A.
*Calyx shape.*—Five-lobed.
*Calyx length.*—Approximately 3 mm. in length.
*Calyx diameter.*—Approximately 6 mm. in diameter.
*Sepal shape.*—Linear.
*Sepal apex.*—Acute.
*Sepal margin.*—Entire.
*Sepal surface.*—Slightly pubescent.
*Sepal color.*—138B.
*Flower longevity.*—Flowers last 2–3 weeks.
Reproductive organs (Androecium) only visible when retracting palate:
*Stamen number.*—Two in number.
*Anther dimensions.*—Less than 1 mm. in length and width.
*Anther color.*—160B.
*Pollen color.*—160B.
*Amount of pollen.*—Low.
Reproductive organs (Gynoecium) only visible when retracting palate.
*Pistil dimensions.*—Approximately 1 mm. in length and width.
*Style dimensions.*—Approximately 1 mm. in length and width.
*Style color.*—144A.
*Stigma color.*—144A.
*Ovary color.*—155D.
Seed production:
*Quantity of seed.*—15 fertile seeds per capsule.
*Quantity of capsules.*—20 per flowering spike.
*Capsule dimensions.*—12 mm. in length and 7 mm. in width.
*Capsule color.*—177D.
*Capsule surface.*—Glossy.
*Appearance of seed.*—Flattened and winged.
*Seed color.*—200D and wing 156D.
*Shape of seed.*—Oval.
*Seed dimensions.*—3 mm. in length and 2.5 mm. in width.

I claim:

1. A new and distinct cultivar of Nemesia plant named 'Pensug' as described and illustrated.

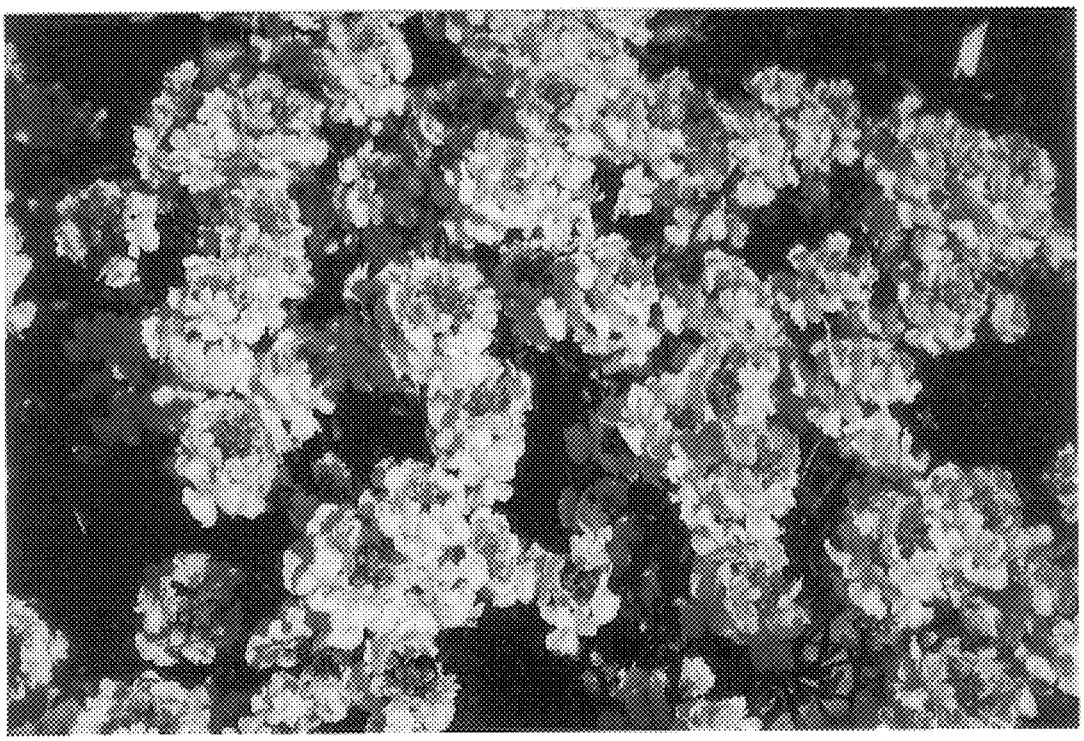

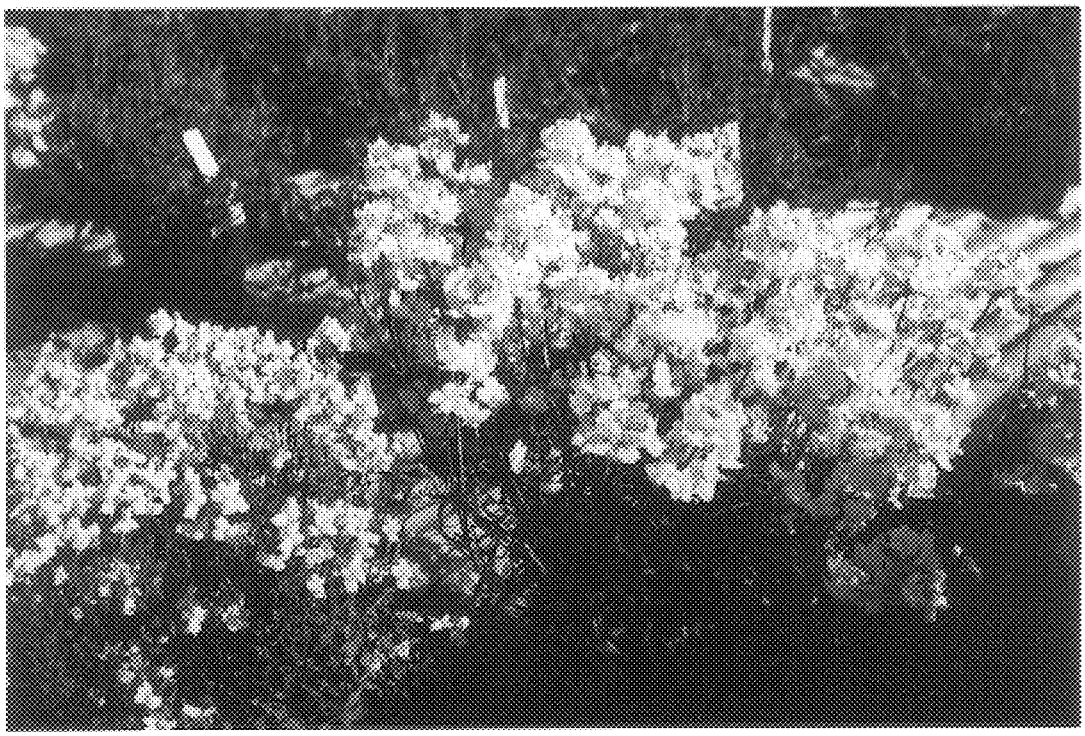

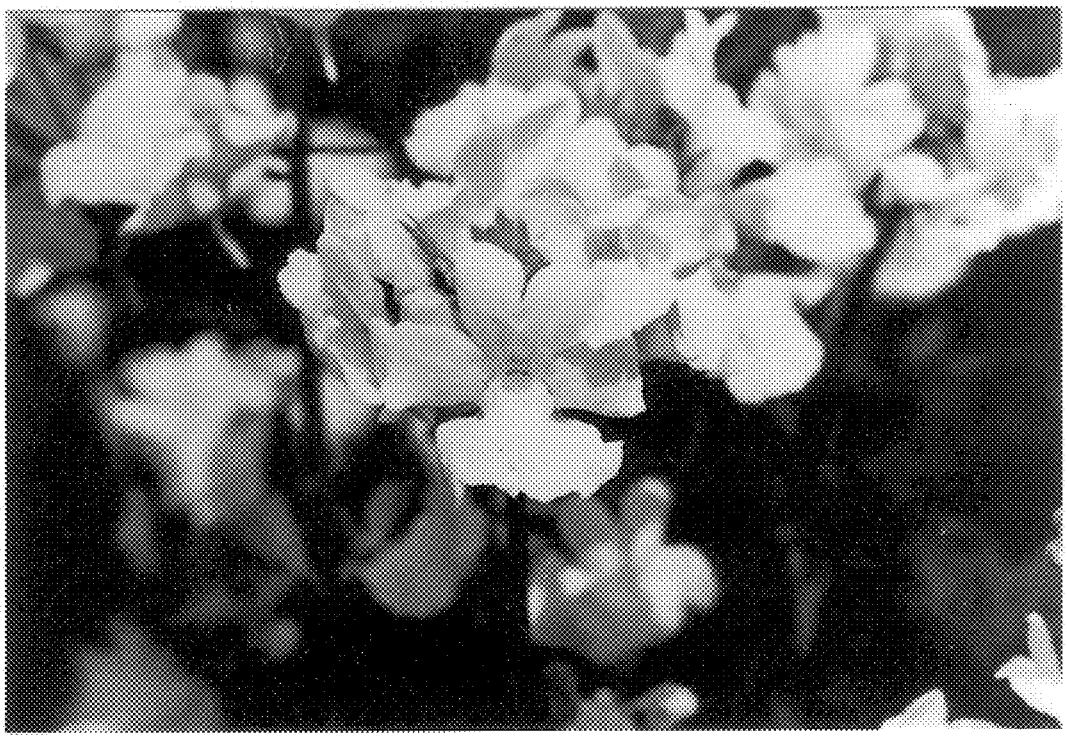

* * * * *